United States Patent
Betley et al.

(10) Patent No.: US 7,960,182 B2
(45) Date of Patent: Jun. 14, 2011

(54) AFFINITY ADSORBENTS FOR FACTOR VIII AND VON WILLEBRAND'S FACTOR

(75) Inventors: Jason Richard Betley, Herts (GB); Baldev Singh Baines, Cambridge (GB)

(73) Assignee: Prometic Biosciences Ltd., Isle of Man, British Isles (GB)

( * ) Notice: Subject to any disclaimer, the term of this patent is extended or adjusted under 35 U.S.C. 154(b) by 158 days.

(21) Appl. No.: 11/913,508

(22) PCT Filed: May 9, 2006

(86) PCT No.: PCT/GB2006/001693
§ 371 (c)(1), (2), (4) Date: Nov. 2, 2007

(87) PCT Pub. No.: WO2006/120427
PCT Pub. Date: Nov. 16, 2006

(65) Prior Publication Data
US 2009/0275141 A1     Nov. 5, 2009

(30) Foreign Application Priority Data

May 9, 2005   (GB) ................................. 0509443.8

(51) Int. Cl.
*G01N 30/00*   (2006.01)
(52) U.S. Cl. .......... 436/178; 436/177; 436/161; 436/86; 436/63; 544/180; 544/194; 544/204; 544/212
(58) Field of Classification Search .......................... None
See application file for complete search history.

(56) References Cited

FOREIGN PATENT DOCUMENTS

| EP | 0 411 810 | 2/1991 |
|---|---|---|
| WO | WO 9710887 A1 * | 3/1997 |
| WO | WO 00/67900 | 11/2000 |

OTHER PUBLICATIONS

Berg, Axel et al. "Dye-ligand centrifugal affinity chromatography." Bioseparation (1990) 1 p. 23-31.*
Burton et al., "Design of Novel Affinity Adsorbents for the Purification of Trypsin-like Proteases," *Journal of Molecular Recognition*, 1992, vol. 5, pp. 55-68.
Lowe, "Combinatorial approaches to affinity chromatography," *Current Opinion in Chemical Biology*, 2001, vol. 5, pp. 248-256.

* cited by examiner

*Primary Examiner* — Yelena G Gakh
*Assistant Examiner* — Christopher A Hixson
(74) *Attorney, Agent, or Firm* — Saliwanchik, Lloyd & Eisenschenk

(57) ABSTRACT

For the separation, removal, isolation, purification, characterization, identification or quantification of Factor VIII, von Willebrand's Factor or a protein that is a analogue of either, an affinity adsorbent is used that is a compound of formula (II) wherein one X is N and the other is N, C—Cl or C—CN; A is a support matrix, optionally linked to the triazine ring by a spacer; Y is O, S or $NR_2$; Z is O, S or N—$R_3$; $R_2$ and $R_3$ are each H, $C_{1-6}$ alkyl, $C_{1-6}$ hydroxyalkyl, benzyl or β-phenylethyl; B and W are each an optionally substituted hydrocarbon linkage containing from 1 to 10 carbon atoms; D is H, OH or a primary amino, secondary amino, tertiary amino, quaternary ammonium, imidazole, guanidino or amidino group; or B-D is —CHCOOH—$(CH_2)_{3-4}$—$NH_2$; and $R_7$ is a group bearing a positive charge at neutral pH.

8 Claims, No Drawings

AFFINITY ADSORBENTS FOR FACTOR VIII AND VON WILLEBRAND'S FACTOR

This application is a National Stage Application of International Application Number PCT/GB2006/001693, filed May 9, 2006; which claims priority to Great Britain Application No. 0509443.8, filed May 9, 2005.

FIELD OF THE INVENTION

This invention relates to compounds and their use as affinity ligands.

BACKGROUND OF THE INVENTION

Factor VIII (previously known as antihaemophilic factor) is a glycoprotein found in circulating plasma at levels of ~200 ng/mL. The naturally occurring mature single chain protein has a heterogeneous molecular weight of between 265 and 270 kDa depending on glycosylation, though a wider range of 170-280 kDa molecular weight proteins are observed in plasma depending on allelic variation, glycosylation, modification, is fragmentation in vivo. A number of recombinant Factor VIII products is available, and also vary considerably in protein structure and molecular weight.

Plasma Factor VIII has the additional complicating factor that it exists in close association with von Willebrand's Factor (vWF), a complex multimeric protein also involved in clotting. vWF itself is of therapeutic utility, either alone or in conjunction with Factor VIII.

Factor VIII participates in a complex clotting cascade culminating in the conversion of vWF/FVIII to fibrin, and the formation of a fibrin clot. Genetic abnormalities in the production of Factor VIII result in the disease Haemophilia A, which manifests itself primarily in repeated bleeding episodes due to reduced or absent clot formation. Haemophilia A and its symptoms (such as uncontrolled bleeding) can be treated with plasma-derived or recombinant Factor VIII. With appropriate dosing, prophylactic use of Factor VIII can markedly reduce the number and severity of bleeding episodes, including those observed during surgery.

Purification of Factor VIII/vWF from plasma or Factor VIII from recombinant sources is a complex process, generally involving a number of chromatographic and/or precipitation and/or viral inactivation steps. Purification from plasma additionally often involves initial cryoprecipitation and reconstitution steps. These complex purification procedures, coupled with inherent protein instability, result in poor yields of purified product. Immunoaffinity chromatography has been described, but aside from its inherent costliness, the chromatography materials used suffer from a lack of stability and cleanability, resulting in very limited re-use. Peptide ligand-based media suffer from similar problems as immunoaffinity media, and have not found widespread acceptance. It would be desirable to obtain a chromatography material capable of isolating Factor VIII or Factor VIII/von Willebrand's Factor from a number of sources in a yield, purity, and cost-effectiveness heretofore not possible.

WO97/10887 discloses triazine-based compounds, useful as affinity adsorbents, of formula I

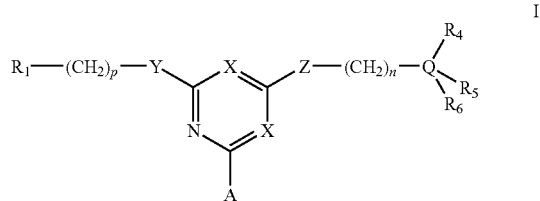

wherein $R_1$ is H, alkyl, hydroxyalkyl, cyclohexyl, $NH_2$, phenyl, naphthyl, 1-phenylpyrazole, indazole, benzthiazole, benzoxazole or benzimidazole, any of which aromatic groups can be substituted with one or more of alkyl, alkoxy, acyloxy, acylamino, amino, $NH_2$, OH, $CO_2H$, sulphonyl, carbamoyl, sulphamoyl, alkylsulphonyl and halogen;

one X is N and the other is N, C—Cl or C—CN;

Y is O, S or $NR_2$;

Z is O, S or $NR_3$;

$R_2$ and $R_3$ are each H, alkyl, hydroxyalkyl, benzyl or β-phenylethyl;

Q is benzene, naphthalene, benzthiazole, benzoxazole, 1-phenylpyrazole, indazole or benzimidazole;

$R_4$, $R_5$ and $R_6$ are each H, OH, alkyl, alkoxy, amino, $NH_2$, acyloxy, acylamino, $CO_2H$, sulphonic acid, carbamoyl, sulphamoyl, alkylsulphonyl or halogen;

n is 0 to 6;

p is 0 to 20; and

A is a support matrix, optionally linked to the triazine ring by a spacer.

Compounds of formula I are disclosed as having affinity for proteins such as immunoglobulins, insulin, Factor VII or human growth hormone.

Compounds of related structure are disclosed in WO00/67900 and WO03/097112. They have affinity for endotoxins.

SUMMARY OF THE INVENTION

Surprisingly, it has been found that certain compounds, many of which are novel, are useful for affinity-based isolation of vWF/FVIII. These compounds are of formula II

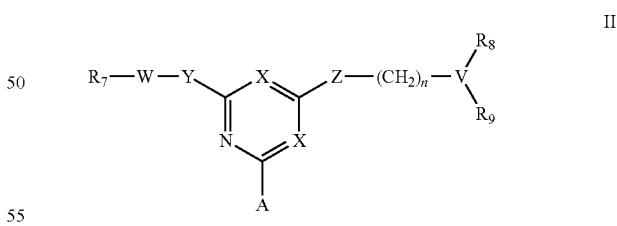

wherein X, Y, Z, n and A are as defined for formula I above;

$R_7$ is a group bearing a positive charge at neutral pH;

W is an optional linker;

V is as described above for Q, but alternatively may be a nodal structure; and $R_8$ and $R_9$ are as defined for $R_4$, $R_5$ and $R_6$, but additionally include cyclic structures, or $R_8$ and $R_9$ are linked to form such a cyclic structure.

Further, compounds of the invention include the corresponding ligands, in which A is replaced by a functional group, linked directly or indirectly to the triazine ring, which can be immobilised on a support matrix. The terms "ligand" and "adsorbent" may be used interchangeably, below.

DESCRIPTION OF THE INVENTION

WO97/10887, WO00/67900 and WO03/097112 disclose how combinatorial libraries of ligands can be built on a solid support. Their disclosures, including examples of embodiments and procedures common to the present invention, are incorporated herein by reference. During the screening of a set of these combinatorial libraries with pooled human plasma as feedstock, a number of ligands were identified as being capable of selectively binding and eluting human vWF/FVIII.

Compounds of formula II, for use in the invention, can be prepared by procedures known to those skilled in the art. Such procedures are described in the 3 PCT publications identified above; they can be readily adapted to the preparation of new compounds.

WO97/10887 gives examples of A, including spacers or linkers L via which the triazine ring may be linked to a solid support M. As described in WO97/10887, such supports include agarose, sepharose, silica, cellulose, dextran, starch, alginate, carrageenan, synthetic polymers, glass and metal oxides. Such materials may be activated before reaction to form an adsorbent of this invention.

L may be, for example, $-T-(-V^1-V^2)_m-$, wherein

T is O, S or $-NR^7-$;

m is 0 or 1;

$V^1$ is an optionally substituted hydrocarbon radical of 2 to 20 C atoms; and $V^2$ is O, S, $-COO-$, $-CONH-$, $-NHCO-$, $-PO_3H-$, $-NH$-arylene-$SO_2-CH_2-CH_2-$ or $-NR_8-$; and $R^7$ and $R^8$ are each independently H or $C_{1-6}$ alkyl.

In compounds of the invention, $R_7$ is preferably a secondary, or more preferably, tertiary amine e.g. of the formula $NR_{10}R_{11}$ wherein $R_{10}$ and $R_{11}$ are each independently $C_{1-6}$ alkyl (such as ethyl), or $NR_8R_9$ forms a ring, or one of $R_{10}$ and $R_{11}$ forms a ring together or with an atom in the linker W. The linker W may be an alkyl, aromatic or aralkyl linker, e.g. of 2 to 7, preferably 3 to 4, chain atoms, which may itself be substituted, e.g. with an OH group.

The nature of the other "arm" i.e. Z—B-D, may be less critical.

In a preferred embodiment of the invention, the vWF/FVIII-binding adsorbent is represented by structure III

III

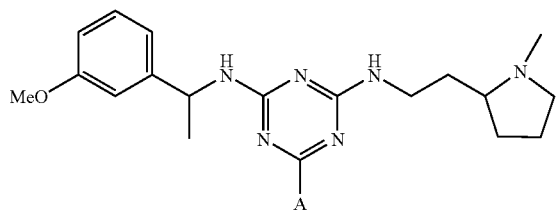

In a further preferred embodiment of the invention, the vWF/FVIII-binding adsorbent is represented by structure IV (protonated at physiological pH)

IV

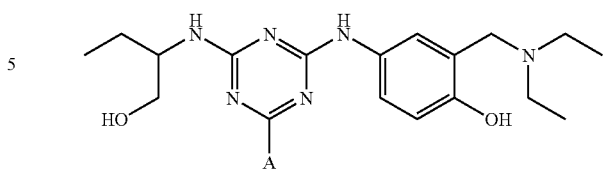

In a most preferred embodiment of the invention, the vWF/FVIII-binding adsorbent is represented by structure V shown below:

V

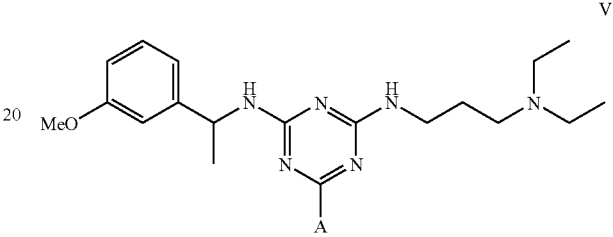

The vWF/FVIII-binding ligands and adsorbents described herein are useful for the purification of vWF/FVIII from complex mixtures including, but not limited to, human plasma and recombinant fermentation supernatants. This utility is demonstrated below in Example 4, by chromatography experiments using human pooled plasma.

The term "vWF/FVIII" is used herein to describe vWF/FVIII itself and also analogues that have the functional characteristics of vWF/FVIII, e.g. in terms of affinity to a given compound described herein. Thus, the analyte may be a protein that is a functional fragment of vWF/FVIII, or a structural analogue having one, more of all of the same binding sites, or a fusion protein.

The following Examples illustrate the invention.

Synthesis of Dichlorotriazinyl-(R)-1-(3-Methoxyphenyl)-ethylamine

Cyanuric chloride (5.0 g) dissolved in acetone (35 mL) was cooled to 0° C., before (R)-1-(3-methoxyphenyl)ethylamine (4.1 g) dissolved in acetone (50 ml) was added dropwise over 30 minutes with cooling, to ensure the temperature did not exceed 5° C. 10 M Sodium hydroxide (2.71 mL) was then added slowly. After 45 minutes, the reaction mixture was added with stirring to iced water (20 g). The oily product was extracted into dichloromethane (150 mL), dried over anhydrous magnesium sulphate, and evaporated to afford the product as a yellow oil (7.96 g).

Example 1

Synthesis of Adsorbent V

To amino-Sepharose CL-4B (475 g weight settled in water—16 μmol/g substitution) was added dimethylformamide (DMF) (475 mL). Di-isopropylethylamine (4.37 mL) was added, the mixture stirred over 15 minutes before dichlorotriazinyl-(R)-1-(3-methoxyphenyl)-ethylamine (7.57 g) dissolved in DMF (250 mL) was added to the reaction mixture. The mixture was stirred over 3 hours before the gel was washed with 70% aqueous DMF (4×500 mL), 50% aqueous DMF (2×500 mL), and water (11×500 mL). To 150 g (settled) of this material slurried in water (75 mL) and added portionwise to a solution of N,N-diethyl-1,3-propanediamine (3.8 mL) in water (75 mL) at 60° C. After addition, the mixture was warmed again to 60° C., and stirred at this temperature over 19 hours. The gel was then filtered off and washed with water (12×150 mL), before storage in 20% aqueous ethanol preservative.

Example 2

Synthesis of Adsorbent III

The intermediate gel product from Example 2 (150 g settled) was slurried in water (75 mL) and added portionwise to a solution of 2-(2-aminoethyl)-1-methylpyrrolidine (3.5 mL) in water (75 mL) at 60° C. After addition, the mixture was warmed again to 60° C., and stirred at this temperature over 19 hours. The gel was then filtered off and washed with water (12×150 mL), before storage in 20% aqueous ethanol preservative.

Example 3

Synthesis of Adsorbent IV

To amino-Sepharose CL-4B (100 g weight settled in water—16 µmol/g substitution) was suspended in 1 M potassium phosphate pH 7.0 (100 mL), then allowed to drain. To this gel was then added 1 M potassium phosphate pH 7.0 (25 mL), and RO water (250 mL). The slurry was stirred vigorously while acetone (50 mL) was added. After cooling in an ice/salt bath over 30 minutes, cyanuric chloride (2.5 g) in cold acetone (25 mL) was added in one portion. The mixture was stirred at 0° C. over 1 hour, before being washed with 50% aqueous acetone (5×100 mL), RO water (5×100 mL), 50% aqueous acetone (5×100 mL), and RO water (10×100 mL). This settled gel was then slurried with 50% aqueous DMF (100 mL) containing 2-aminobutanol (1 g), at room temperature over 4 hours. The slurry was filtered, then washed 50% aqueous DMF (5×100 mL) and RO water (10×100 mL). This settled gel was then slurried with 50% aqueous DMF (100 mL) containing 4-amino-a-diethylamino-o-cresol dihydrochloride (4.2 g), and adjusted to pH 9 with sodium hydroxide (10 M), and stirred at 60° C. overnight. The slurry was filtered, then washed 50% aqueous DMF (5×100 mL) and RO water (10×100 mL). The gel was incubated in a final concentration of 0.5 M NaOH/25% ethanol for 3 days at 40° C., then washed with 0.5 M NaOH/25% ethanol (5×100 mL), then RO water (10×100 mL). After the final wash was allowed to drain under gravity, 1.0 M NaOH (100 mL) was added and the mixture incubated at 40° C. for 3 days. The gel was then washed with 0.5 M NaOH (5×100 mL), then RO water (10×100 mL). After washing with 0.1 M PBS pH 7.0 (3×100 mL), the gel was washed a further time with RO water (10×100 mL), before storage in the cold room at 4° C. in 20% v/v aqueous ethanol.

Example 4

Example of Chromatography on Human Plasma with Adsorbent V

Chromatography experiments were performed using a 1.6 cm diameter XK16/20 column with a 20 mL column volume using a low-pressure chromatography system (Kipp & Zonen flat bed chart-recorder, Gilson minipuls 3 peristaltic pump and Gilson UV detector). The column was equilibrated with 5 column volumes of 20 mM Tris.HCl, 20 mM sodium citrate, 140 mM sodium chloride pH 7.5 at 80 cm/hr. Human source plasma was treated with 20 mM Tris.HCl and 100 mM sodium chloride (final concentration). 200 mL of treated plasma was 10 µm filtered then loaded at 80 cm/hr. Post-load wash was with 20 mM Tris.HCl, 20 mM sodium citrate, and 140 mM sodium chloride pH 7.5 to baseline absorbance. The column was then eluted with. 20 mM Tris.HCl, 20 mM sodium citrate, 3 mM CaCl2, 30% Ethylene Glycol and 500 mM sodium chloride and 0.01% Tween 80 pH 7.5. Post elution the column was sanitised with 8 M Urea pH 7.0. The column was subsequently cleaned with 0.5 M sodium hydroxide. Load, non-bound, and elution fractions were analysed by nephelometry, vWF ELISA and Factor VIII Chromogenic activity assay to determine recoveries. SDS PAGE was also carried out to investigate purity.

Recovery is reported in Table 1.

TABLE 1

| Recovery of vWF/FVIII from chromatography with adsorbent V | | | |
|---|---|---|---|
| Load | vWF | 1632 µg | |
| | F VIII | 147 IU | |
| | | | (% Recovery) |
| Non-bound | vWF | 512 µg | 32 |
| | F VIII | 29.2 IU | 20 |
| | | | (% Recovery) |
| Elution | vWF | 879 µg | 54 |
| | F VIII | 79 IU | 54 |

The Factor VIII result was determined by chromogenic activity assay (COATEST VIII: C/4 supplied by Chromogenix). Results are in international units (IU) where normal human plasma contains 1 international unit of factor VIII activity per mL.

The vWF result was determined by ELISA.

The invention claimed is:

1. A method for binding an analyte consisting essentially of Factor VIII, von Willebrand's Factor or a protein that is an analogue of either, wherein the analogue is a functional fragment of Factor VIII or von Willebrand's Factor, a structural analogue having one or more of the same binding sites of Factor VIII or von Willebrand's Factor, or a fusion protein comprising Factor VIII, von Willebrand's Factor, a functional fragment, or a structural analogue thereof, wherein said method comprises providing an affinity adsorbent material comprising a support matrix having covalently attached to its surface in sufficient quantity to act as an effective adsorbent material a compound having the following structure:

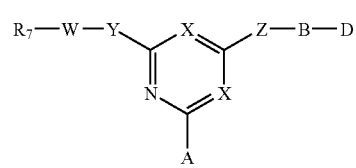

II wherein each X is N;
A is a support matrix, optionally linked to the triazine ring by a spacer;
Y is O, S or $NR_2$;
Z is O, S or $N-R_3$;

$R_2$ and $R_3$ are each H or $C_{1-6}$ alkyl;

B is an optionally substituted hydrocarbon linkage containing from 1 to 10 carbon atoms;

W is an optionally substituted hydrocarbon chain containing up to 4 carbon atoms in the hydrocarbon chain;

D is H, OH or a primary amino, secondary amino, tertiary amino, quaternary ammonium, imidazole, guanidino or amidino group; or B-D is —CHCOOH—$(CH_2)_{3-4}$—$NH_2$; and $R_7$ is a tertiary amine group bearing a positive charge at neutral pH; and contacting a sample containing the analyte so that the analyte binds to the affinity adsorbent material.

2. The method of claim 1, wherein the affinity adsorbent material is packed in a chromatography column, and further comprising the steps of eluting the column under conditions in which the analyte is released from the adsorbent material and collecting the analyte.

3. The method of claim 2, further comprising analyzing the analyte after it is collected and wherein the subsequent analysis comprises an analysis procedure selected from the group consisting of nephelometry, ELISA, Factor VIII chromogenic activity assay, and SDS PAGE.

4. The method, according to claim 1, wherein Y and Z are each NH.

5. The method, according to claim 1, wherein the hydrocarbon chain of W has 2 to 4 carbon atoms.

6. The method, according to claim 1, wherein the adsorbent is of formula III:

7. The method, according to claim 1, wherein the adsorbent is of formula IV:

8. The method, according to claim 1, wherein the adsorbent is of formula V:

* * * * *